US010449044B2

(12) United States Patent
Anderson (10) Patent No.: US 10,449,044 B2
(45) Date of Patent: Oct. 22, 2019

(54) TRANSCATHETER VALVE DELIVERY SYSTEM WITH SEPTUM HOLE CLOSURE TIP ASSEMBLY

(71) Applicant: Medtronic Vascular, Inc., Santa Rosa, CA (US)

(72) Inventor: Marc Anderson, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 288 days.

(21) Appl. No.: 15/609,203

(22) Filed: May 31, 2017

(65) Prior Publication Data

US 2017/0348096 A1 Dec. 7, 2017

Related U.S. Application Data

(60) Provisional application No. 62/344,869, filed on Jun. 2, 2016.

(51) Int. Cl.
*A61F 2/24* (2006.01)
*A61B 17/00* (2006.01)
*A61B 17/34* (2006.01)

(52) U.S. Cl.
CPC .......... *A61F 2/243* (2013.01); *A61B 17/0057* (2013.01); *A61F 2/2412* (2013.01);
(Continued)

(58) Field of Classification Search
CPC ............ A61B 17/0057; A61B 17/3468; A61B 2017/00247; A61B 2017/00575;
(Continued)

(56) References Cited

U.S. PATENT DOCUMENTS 5,957,949 A * 9/1999 Leonhardt ................ A61F 2/07
606/108
8,105,375 B2 1/2012 Navia et al.
(Continued)

FOREIGN PATENT DOCUMENTS

| WO | WO2013/096541 | 6/2013 |
| WO | WO2015/075128 | 5/2015 |
| WO | WO2015/165117 | 11/2015 |

OTHER PUBLICATIONS

PCT/US2017/035304, The International Search Report and The Written Opinion of the International Searching Authority, dated Aug. 3, 2017.

*Primary Examiner* — Ryan J. Severson
(74) *Attorney, Agent, or Firm* — Dicke, Billig & Czaja, PLLC (57) ABSTRACT

Transcatheter heart valve delivery systems having a tip assembly configured to close the hole or perforation made in a patient's septal wall after transseptal delivery of a stented prosthetic heart valve to a defective heart valve (e.g., a mitral valve). The delivery device is configured to permit in vivo release of the tip assembly immediately after deployment of the stented prosthetic heart valve to implant the tip assembly into the septal wall proximate the hole through which the stented prosthetic heart valve is delivered. Methods of treating the defective heart valve, including closing the hole made during transseptal delivery of the stented prosthetic heart valve with the tip assembly of the delivery device are also disclosed.

20 Claims, 5 Drawing Sheets

(52) U.S. Cl.
CPC ........ *A61F 2/2436* (2013.01); *A61B 17/3468* (2013.01); *A61B 17/3478* (2013.01); *A61B 2017/0061* (2013.01); *A61B 2017/00243* (2013.01); *A61B 2017/00247* (2013.01); *A61B 2017/00575* (2013.01); *A61B 2017/00579* (2013.01); *A61B 2017/00588* (2013.01); *A61B 2017/00619* (2013.01); *A61B 2017/00623* (2013.01); *A61F 2220/0016* (2013.01)

(58) Field of Classification Search
CPC ........... A61B 2017/00579; A61B 2017/00588; A61B 2017/0061; A61B 2017/00615; A61B 2017/00619; A61B 2017/00623; A61B 2017/00628; A61F 2/2427; A61F 2/243; A61F 2/2436; A61F 2220/0016
See application file for complete search history.

(56) References Cited

U.S. PATENT DOCUMENTS

| | | | | |
|---|---|---|---|---|
| 8,137,398 | B2 * | 3/2012 | Tuval | A61F 2/2418 623/2.17 |
| 8,157,852 | B2 * | 4/2012 | Bloom | A61F 2/2412 623/1.11 |
| 8,313,525 | B2 * | 11/2012 | Tuval | A61F 2/2418 623/2.11 |
| 8,979,922 | B2 * | 3/2015 | Jayasinghe | A61F 2/2418 623/2.11 |
| 9,526,483 | B2 * | 12/2016 | Tuval | A61B 17/0057 |
| 9,579,198 | B2 * | 2/2017 | Deem | A61F 2/243 |
| 9,592,120 | B2 * | 3/2017 | Tuval | A61F 2/2418 |
| 9,730,792 | B2 * | 8/2017 | Lutter | A61F 2/2457 |
| 9,848,880 | B2 * | 12/2017 | Coleman | A61F 2/2457 |
| 2004/0260394 | A1 | 12/2004 | Douk et al. | |
| 2007/0185571 | A1 * | 8/2007 | Kapadia | A61B 17/00234 623/2.11 |
| 2008/0243245 | A1 * | 10/2008 | Thambar | A61F 2/2418 623/2.11 |
| 2011/0245911 | A1 * | 10/2011 | Quill | A61F 2/2418 623/1.26 |
| 2012/0016411 | A1 * | 1/2012 | Tuval | A61B 17/0057 606/213 |
| 2014/0358222 | A1 * | 12/2014 | Gorman, III | A61F 2/2409 623/2.11 |
| 2015/0142101 | A1 * | 5/2015 | Coleman | A61F 2/2457 623/2.11 |
| 2015/0297346 | A1 * | 10/2015 | Duffy | A61F 2/2436 623/2.11 |
| 2016/0345943 | A1 * | 12/2016 | Cui | A61B 17/0057 |
| 2017/0348096 | A1 * | 12/2017 | Anderson | A61F 2/243 |
| 2018/0153691 | A1 * | 6/2018 | Anderson | A61F 2/2433 |
| 2018/0207011 | A1 * | 7/2018 | Rothstein | A61F 2/962 |

* cited by examiner

TRANSCATHETER VALVE DELIVERY SYSTEM WITH SEPTUM HOLE CLOSURE TIP ASSEMBLY

CROSS-REFERENCE TO RELATED APPLICATIONS

This Non-Provisional Patent Application claims the benefit of the filing date of U.S. Provisional Patent Application Ser. No. 62/344,869, filed Jun. 2, 2016, entitled "Transcatheter Valve Delivery System with Septum Hole Closure Tip Assembly," the entire teachings of which are incorporated herein by reference.

BACKGROUND

The present disclosure relates to delivery systems for delivering a stented prosthetic heart valve, such as a prosthetic mitral valve. More particularly, it relates to transcatheter heart valve delivery systems having a deployable tip assembly, for example, to close a cardiac septum hole or perforation.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With one type of stented prosthetic heart valve designs, the stent frame is formed to be self-expanding. The valved stent is crimped down to a desired size and held in that compressed state within a sheath or by other means for transluminal delivery. Retracting the sheath (or other release operation) from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety. Another type of valve stent can be initially provided in an expanded or uncrimped condition, then crimped or compressed about a balloon portion of a catheter. The balloon is subsequently inflated to expand and deploy the prosthetic heart valve.

The actual shape and configuration of any particular transcatheter prosthetic heart valve is dependent, at least to some extent, upon the valve being replaced or repaired (e.g., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles.

Other anatomical-based constraints may be placed on the transcatheter delivery system, such as size and/or length. For example, when accessing certain valves via certain approach techniques, deployment of a conventionally-compressed and delivered prosthetic heart valve may be difficult due to anatomical space limitation (e.g., when accessing the mitral valve via trans-septal approach, limited space may be available in the left atrium for locating and manipulating the delivery system in effectuating prosthetic valve deployment). These anatomical constraints can be more difficult to address with larger stented prosthetic valve designs.

Another significant delivery obstacle in trans-septal delivery of a prosthetic heart valve is the septal wall. In order to provide passage of the prosthetic heart valve and the delivery device through the septal wall, a hole in the septal wall is formed. In some situations, this hole can be larger than practitioners believe is safe to leave in the septal wall and in these cases, the hole needs to be closed at the end of the procedure.

The present disclosure addresses problems and limitations associated with the related art.

SUMMARY

Aspects of the disclosure are directed to a delivery device that is configured to deliver and deploy a stented prosthetic heart valve to a defective native heart valve, such as a mitral valve. The delivery device can include a delivery sheath assembly, a support shaft assembly and a tip assembly. The delivery device is configured to provide a loaded state in which the stented prosthetic heart valve is compressed over the support shaft assembly and retained within a capsule of the delivery sheath assembly. The tip assembly is configured to provide a delivery state in which the tip assembly is compacted for delivery through a patient's vasculature and septal wall and also an expanded deployed state for occluding a hole in the septal wall through which the delivery device was inserted during delivery of the stented prosthetic heart valve. After the stented prosthetic heart valve is implanted at the defective valve, the tip assembly is positioned adjacent the hole and released from the support shaft assembly. Once in position, the tip assembly can transition from the delivery state to the deployed state. In the deployed state, at least one end of the tip assembly expands in diameter to have a diameter that is greater than that of the septum perforation or hole. To maintain the tip assembly in place, occluding the hole, each arm can include one or more barbs attached to and extending therefrom. The barbs are configured to engage tissue proximate the hole after transition to the deployed state. Once secured in place, the tip assembly is detached from the support shaft assembly and left within the septal wall as the other components of the delivery device are withdrawn from the patient.

Aspects of the disclosure also are also directed to methods of treating a defective heart valve (e.g., a mitral valve) including closing the hole in the septal wall with the delivery device after the deployment of the stented prosthetic heart valve with the same delivery device prior to removal of the delivery device. One example method generally includes forming a hole in a septal wall of a heart of the patient, directing a distal region of the delivery device through the hole, deploying the stented prosthetic heart valve from the delivery device to implant the stented prosthetic heart valve at the defective heart valve, and implanting the tip assembly of the delivery device at the hole in the septal wall to occlude the hole. The remaining components of the delivery device proximal the tip assembly are disconnected from the tip assembly and withdrawn from the patient, leaving the tip assembly implanted in the septal wall. Various delivery devices and methods disclosed herein reduce procedure time and complexity.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted stented prosthetic heart valve, the terms "distal" and "outflow" are understood to mean downstream to the direction of blood flow, and the terms "proximal" or "inflow" are understood to mean upstream to the direction of blood flow.

As referred to herein, stented transcatheter prosthetic heart valves (hereinafter "prosthetic valves") useful with and/or as part of the various systems, devices and methods discussed herein may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Prosthetic valves useful with the systems, devices, and methods of the present disclosure can be generally used for replacement of native heart valves (e.g., mitral valves) or to replace a failed bioprosthesis.

In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1:
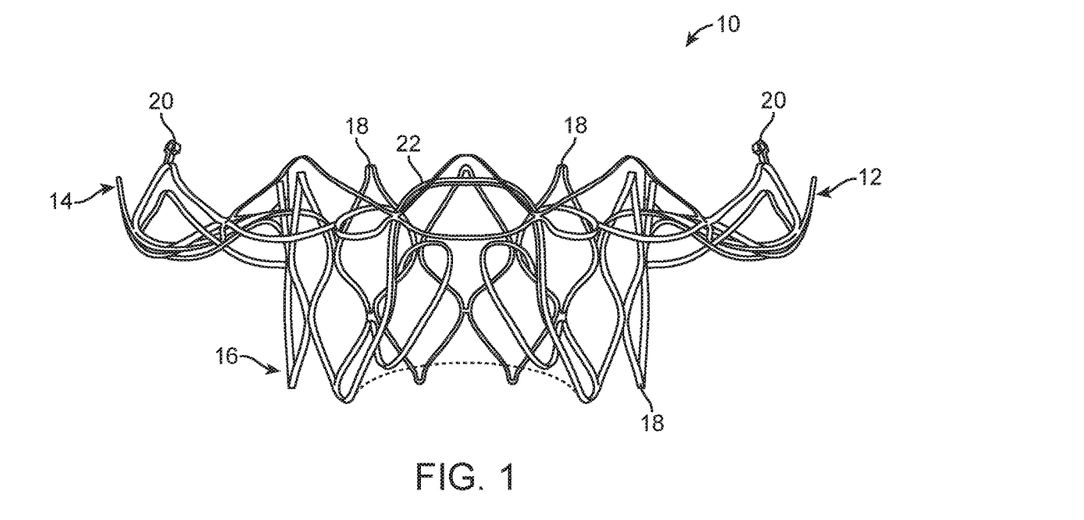
FIG. 1 is a side view of an exemplary stented prosthetic heart valve useful with the devices and methods disclosed herein.

With the above understanding in mind, one simplified, non-limiting example of a prosthetic valve 10 useful with systems, devices and methods of the present disclosure is illustrated in FIG. 1. The prosthetic valve 10 includes a stent or stent frame 12 and a valve structure (not shown) positioned within the stent frame 12. As a point of reference, the prosthetic valve 10 is shown in a normal or expanded condition in the view of FIG. 1. From the normal or expanded condition of FIG. 1, the stent frame 12 can be forced and constrained to the compressed condition during delivery, and will self-expand to the natural condition of FIG. 1 upon removal of the constraining force(s).

The valve structure (not shown) can assume a variety of forms, and can be formed, for example, from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. In some embodiments, the valve structure can be formed, for example, from heart valve tissue, pericardium, and/or other suitable tissue. In some embodiments, the valve structure can include or form one or more leaflets. For example, the valve structure can be in the form of a tri-leaflet bovine pericardium valve, a bi-leaflet valve, or another suitable valve. In some constructions, the valve structure can comprise two or three leaflets that are fastened together at enlarged lateral end regions to form commissural joints, with the unattached edges forming coaptation edges of the valve structure. The leaflets can be fastened to a skirt that in turn is attached to the stent frame 12. The upper ends of the commissure points can designate an inflow portion 14 of the prosthetic valve 10 and the opposite end can designate an outflow portion 16 of the prosthetic valve 10. As reflected in FIG. 1, crowns 18 and/or eyelets 20 (or other shapes) optionally can be formed at one or both of the inflow and outflow portions 14, 16. Further, the stent frame 12 can optionally include or carry additional structural components, such as support arm(s) 22.

Figure 2:
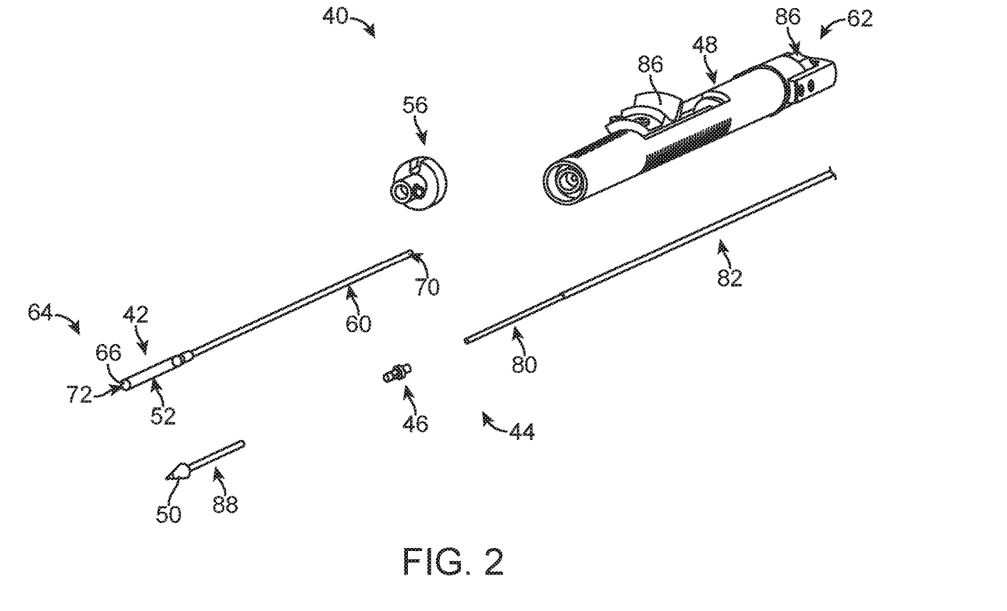
FIG. 2 is a partially exploded, perspective view of an exemplary delivery device for delivering the stented prosthetic heart valve of FIG. 1.
Figure 3:
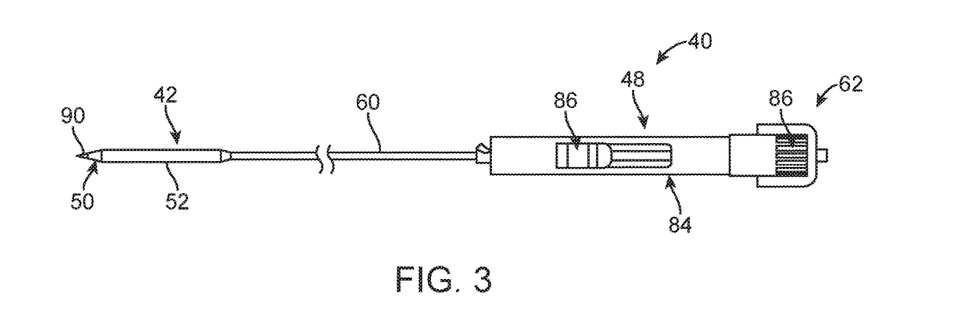
FIG. 3 is a top view of the assembled delivery device of FIG. 2.

One embodiment of a delivery device 40 for percutaneously delivering a prosthetic valve 10 is shown in simplified form in FIGS. 2-3. The delivery device 40 includes the delivery sheath assembly 42, a support shaft or support shaft assembly 44, a handle assembly 48, and a tip assembly 50 releasably connected to the support shaft assembly 44. Details on the various components of the delivery device 40 are provided below. In general terms, however, the delivery device 40 combines with a stented prosthetic heart valve, such as the prosthetic valve 10 of FIG. 1, to form a system for treating a defective heart valve of a patient. The delivery device 40 provides a loaded or delivery state in which the prosthetic valve 10 is loaded over the support shaft assembly 44 and is compressively retained within a capsule 52 of the delivery sheath assembly 42. The support shaft assembly 44 can include a retention assembly or valve retainer 46 which is configured to selectively receive corresponding feature(s) 20 (e.g., paddles, posts, or eyelets) that are provided with the frame 12 of the prosthetic valve 10. The delivery sheath assembly 42 can be manipulated to withdraw the capsule 52 proximally from over the prosthetic valve 10 via operation of the handle assembly 48, permitting the prosthetic valve 10 to self-expand and partially release from the support shaft assembly 44. When the capsule 52 is retracted proximally beyond the valve retainer 54, the prosthetic valve 10 can completely release or deploy from the delivery device 40.

In some embodiments, the delivery sheath assembly 42 defines proximal and distal ends 70, 72, and includes the capsule 52 and an outer sheath 60. The delivery sheath assembly 42 can be akin to a catheter, defining a lumen 66 (referenced generally) that extends from the distal end 72 through the capsule 52 and at least a portion of the outer sheath 60. The capsule 52 extends distally from the outer sheath 60, and in some embodiments has a more stiffened construction (as compared to a stiffness of the outer sheath 60) that exhibits sufficient radial or circumferential rigidity to overtly resist the expected expansive forces of the prosthetic valve 10 when compressed within the capsule 52. For example, the outer sheath 60 can be a polymer tube embedded with a metal braiding, whereas the capsule 52 includes a laser-cut metal tube that is optionally embedded within a polymer covering. Alternatively, the capsule 52 and the outer sheath 60 can have a more uniform or even homogenous construction (e.g., a continuous polymer tube). Regardless, the capsule 52 is constructed to compressively retain the prosthetic valve 10 at a predetermined diameter when loaded within the capsule 52, and the outer sheath 60 serves to connect the capsule 52 with the handle assembly 48. The outer sheath 60 and the capsule 52 are constructed to be sufficiently flexible for passage through a patient's vasculature, yet exhibit sufficient longitudinal rigidity to effectuate desired axial movement of the capsule 52. In other words, proximal retraction of the outer sheath 60 is directly transferred to the capsule 52 and causes a corresponding proximal retraction of the capsule 52. In other embodiments, the outer sheath 60 is further configured to transmit a rotational force or movement onto the capsule 52.

The support shaft or support shaft assembly 44 can have various constructions appropriate for supporting the delivery sheath assembly 42, including indirectly supporting the support shaft assembly 44 (and the prosthetic valve 10 disposed thereon) relative to the capsule 52. In some embodiments, the support shaft assembly 44 includes an intermediate shaft or tube 80 and a proximal shaft or tube 82. The intermediate tube 80 is optionally formed of a flexible polymer material (e.g., PEEK), and is sized to be slidably received within the delivery sheath assembly 42. In some embodiments, the intermediate tube 80 is a flexible polymer tubing (e.g., PEEK) having a diameter slightly less than that of the proximal tube 82. The proximal tube 82 can have a more rigid construction, configured for robust assembly with the handle assembly 48, such as a metal hypotube. Other constructions are also envisioned. For example, in other embodiments, the intermediate and proximal tubes 80, 82 are integrally formed as a single, homogenous tube or shaft.

The support shaft assembly 44 further includes a distal support shaft or distal region 88 connected to the tip assembly 50. The distal support shaft 88 is sized to be slidably received within the lumen 66 of the delivery sheath assembly 42. The distal support shaft 88 can be a flexible polymer tube embedded with a metal braid. Other constructions are also acceptable so long as the distal support shaft 88 exhibits sufficient structural integrity to support the loaded, compressed prosthetic valve 10. The support shaft assembly 44 can define a continuous lumen (not shown) sized to slidably receive an auxiliary component such as a guide wire (not shown).

The handle assembly 48 generally includes a housing 84 and one or more actuator mechanisms 86 (referenced generally). The housing 84 maintains the actuator mechanism(s) 86, with the handle assembly 48 configured to facilitate sliding movement of the delivery sheath assembly 42 relative to other components (e.g., the support shaft assembly 44). The housing 84 can have any shape or size appropriate for convenient handling by a user.

Various features of the components 42, 44, 48 reflected in FIGS. 2-3 and as described herein can be modified or replaced with differing structures and/or mechanisms. Thus, the present disclosure is in no way limited to the delivery sheath assembly 42, the support shaft assembly 44 or the handle assembly 48 as shown and described herein. Any construction that generally facilitates compressed loading of a stented prosthetic heart valve over a support shaft assembly via a retractable outer sheath or capsule is acceptable. Alternatively, the delivery sheath assembly 42 can be omitted from the delivery device 40 if the prosthetic valve 10 is otherwise expandable (e.g., balloon expandable). Further, the delivery device 40 can optionally include additional components or features, such as a flush port assembly 56, a recapture sheath (not shown), etc. The delivery device 40 can also optionally include other components (not shown) that assist or facilitate or control complete deployment of the prosthetic valve 10 and the tip assembly 50.

Figure 4:
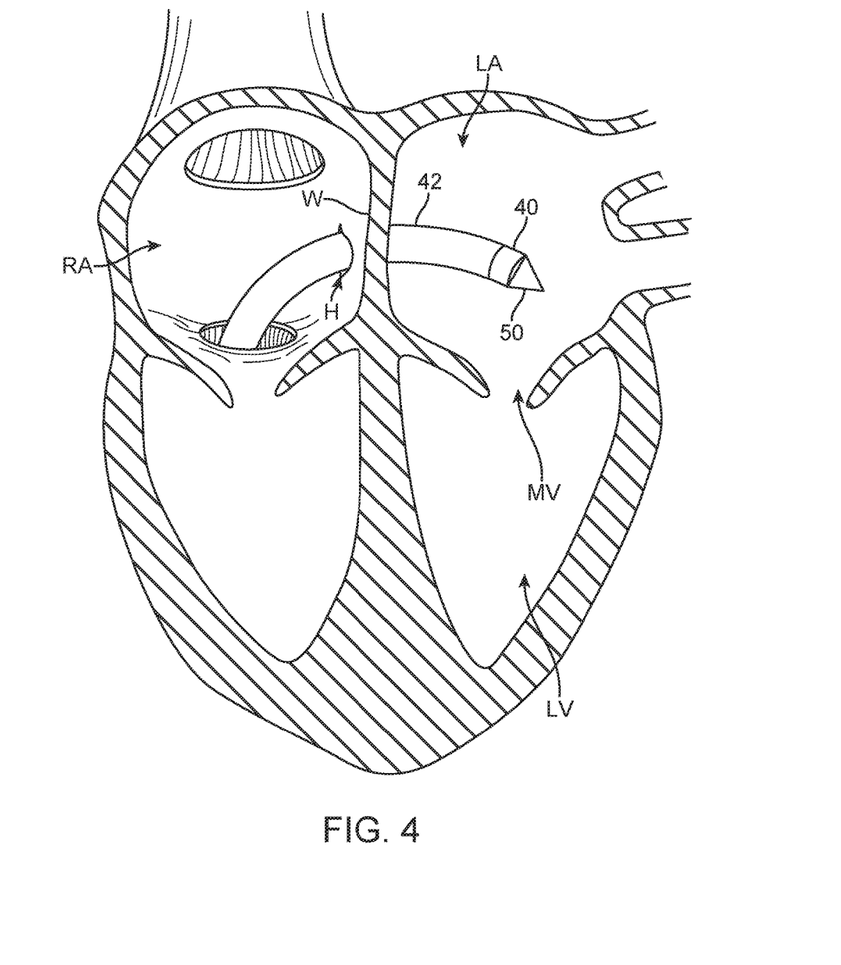
FIG. 4 is a schematic view of the delivery device of FIGS. 2-3 delivering a stented prosthetic heart valve (not visible) through a septal wall to a defective native mitral valve (shown in cross-section).

Referring now also to FIG. 4, which schematically reflects use of the delivery device 40 in a loaded arrangement, delivering the stented prosthetic heart valve 10 (hidden underneath the capsule 52) to the mitral valve MV to repair the defective mitral valve MV. As can be seen, the mitral valve MV separates the left atrium LA and the left ventricle LV. The delivery device 40 is shown after having been introduced into the vasculature via a percutaneous entry point (e.g., the Seldinger technique), and having been tracked through the vasculature and into the left atrium LA. For example, the percutaneous entry point may be formed in a femoral vein. Thereafter, a guide wire (not shown) is advanced through the circulatory system, eventually arriving at the heart. The guide wire is directed into the right atrium RA, traverses the right atrium RA and is made to puncture or otherwise make the hole H, with the aid of a trans-septal needle or pre-existing hole, in the atrial septal wall W, thereby entering the left atrium LA. Once the guide wire is positioned, the endoluminal entry port and the atrial septum hole H are dilated to permit entry of a guide catheter (not shown) and/or the distal end 64 of the delivery device 40 into the left atrium LA. During delivery of the prosthetic valve 10, the arms 102 are collapsed to be longitudinally arranged and generally parallel to the support shaft assembly 44 to reduce a maximum outer diameter D1 of the tip assembly 50. Minimizing the maximum outer diameter D1 of the tip assembly 50 in the delivery state is important for trans-septal delivery as the tip assembly 50 needs to pass through the septal wall W to deliver the prosthetic valve 10 as generally depicted in FIG. 4.

Figure 5:
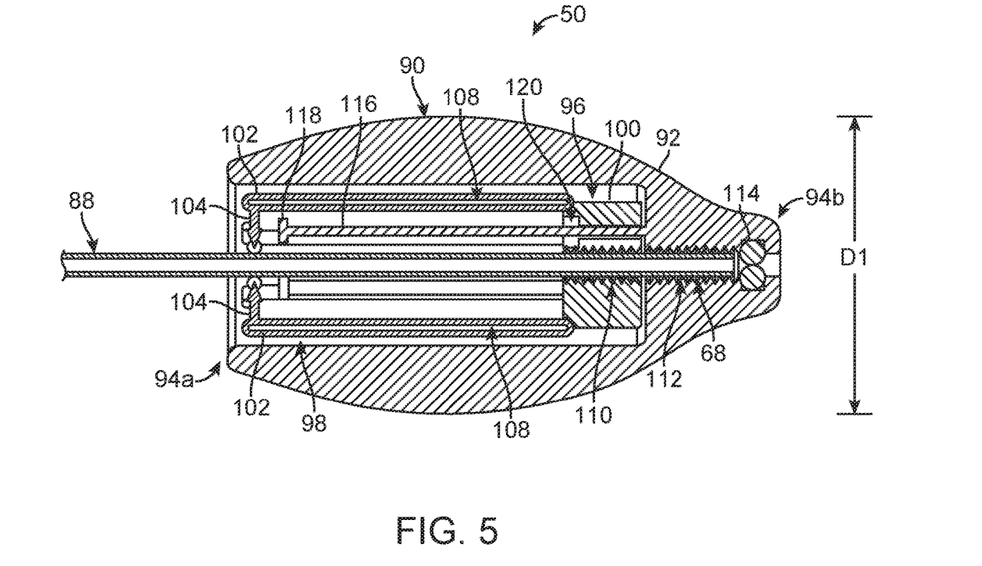
FIG. 5 is a side, cross-sectional view of one exemplary tip assembly of the delivery device of FIGS. 2-3; wherein the tip assembly is shown in an assembled, first delivery state.

With the above general explanations of exemplary procedures and embodiments of the components 42, 44, 48 in mind, portions of one embodiment of the tip assembly 50 are shown in FIG. 5. FIG. 5 generally illustrates the tip assembly 50 in an assembled, collapsed, first delivery state. The tip assembly 50 includes a housing 90 having a distally tapering outer surface 92. The housing 90 further includes proximal and distal ends 94a, 94b, a cavity 96 and an optional seal (e.g., o-ring) 114. Within the cavity 96 is at least one guide rail 116 extending from the distal end 94b of the housing 90 and terminating proximate the proximal end 94a. Each guide rail 116 has an end 118 that is generally T-shaped or otherwise enlarged in diameter at the proximal end 94a of the housing 90 to maintain a connection between an arm assembly 98 and the housing 90 as will be further discussed below.

Figure 6:
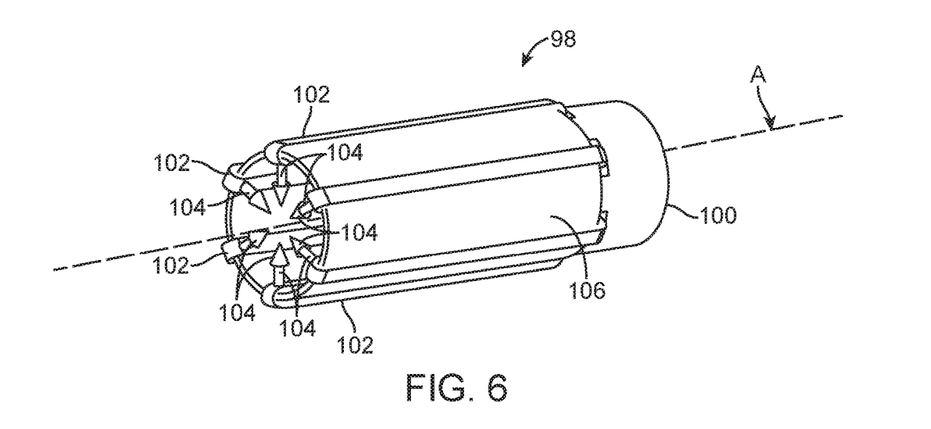
FIG. 6 is a perspective view of an arm assembly of the tip assembly of FIG. 5.

As best shown in FIG. 6, the arm assembly 98 includes a ring 100 having at least one recess 120, a plurality of arms 102 spaced around and radially extending from the ring 100, and a skirt 106 extending between the arms 102. In some embodiments, such as that illustrated, each arm 102 has an opening 108 through which the skirt 106 is woven and supported. Each end 118 of each respective guide rail 116 is positioned within a respective recess 120 of the ring 100 and generally maintains the ring 100 on the guide rail 116 as the end 118 is sized to prevent distal movement of the ring 100 past the recess 120. The guide rails 116 are configured to interface with the arms 102 and prevent the arm assembly 98 from rotating and disengaging from the distal support shaft 88. The arms 102 are pivotally connected to the ring 100 having a memory set shape so that the arms 102 automatically transition from the collapsed, delivery state of FIGS. 5 and 8 to a partially deployed state (FIG. 9) and then to a deployed or expanded state (FIG. 10) once constraining forces collapsing the arms 102 are removed.

Figure 7:
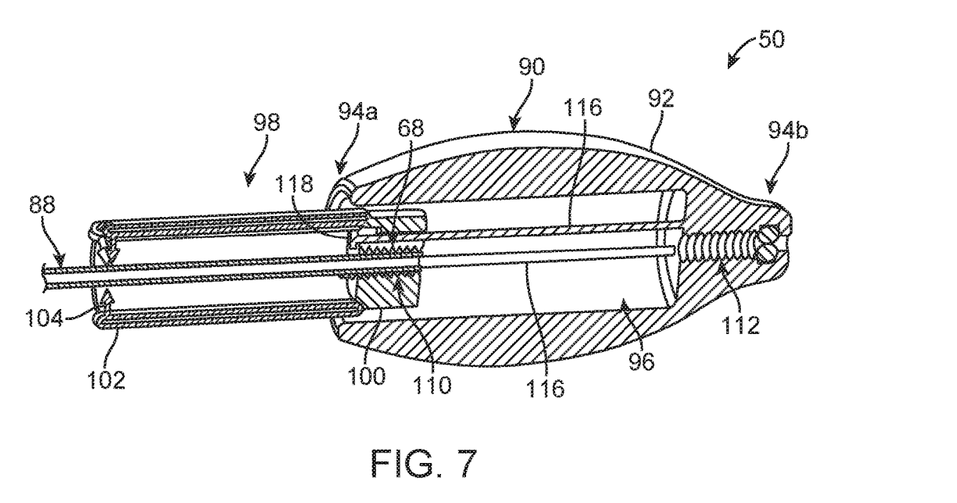
FIG. 7 is a perspective, cross-sectional view of the tip assembly of FIG. 5 partially-assembled.
Figure 8:
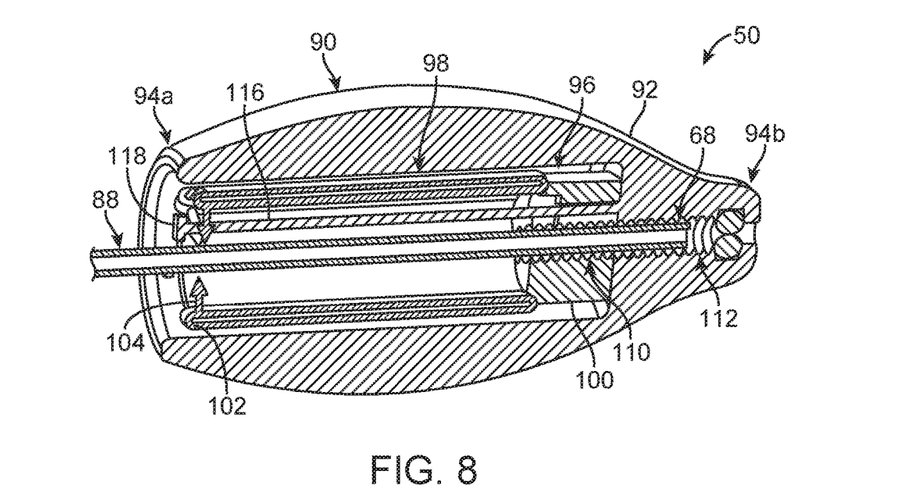
FIG. 8 is a perspective, cross-sectional view of the tip assembly of FIGS. 5 and 7 in an assembled, second delivery state.

FIG. 7 illustrates a partially-assembled tip assembly 50. One way of configuring the delivery device 40 is to provide a plurality of threads 68 on the distal support shaft 88 that correspond to the first threaded aperture 110 within the ring 100. The distal shaft threads 68 are threaded into the first threaded aperture 110 to anchor the arm assembly 98 to the distal support shaft 88. The arm assembly 98 is then pushed distally (as seen in FIG. 7) within the housing 90 to a second threaded aperture 112 in the housing 90 that is coaxially aligned with the first threaded aperture 110 of the ring 100. In this way, the distal support shaft 88 can be threadably connected simultaneously with both the ring 100 and the housing 90 in the delivery state as is generally depicted in FIG. 8 (e.g., about 20% of the distal shaft threads 68 can be connected with the first threaded aperture 110 of the ring 100 and about 80% of the distal shaft threads 68 can be engaged with the second threaded aperture 112 of the housing 90 at the same time). To deploy the tip assembly 50, the distal support shaft 88 is further threaded in the distal direction, away from the ring 100, so that the entirety (i.e. 100%) of the distal shaft threads 68 are engaged with the second threaded aperture 112 as is shown in FIG. 5. This action frees the arm assembly 98 so that a pull-wire or the like (not shown) can pull the arm assembly 98 proximally to the positions of FIGS. 9-10, while the distal support shaft 88 maintains the position of the housing 90. Once the tip assembly 50 is fully deployed and engaged with the septal wall W, the distal support shaft 88 is threaded proximally, through the tip assembly 50, to release the tip assembly 50 from the distal support shaft 88. The tip assembly 50 remains implanted in the septal wall W as the remaining components of the delivery device 40 are withdrawn from the patient.

To engage and maintain the tip assembly 50 adjacent the septal wall W, one or more arms 102 includes a barb 104. In the delivery state, each barb 104 is disposed within the cavity 96 of the housing 84 and in the deployed state, each barb 104 is positioned outside of the cavity 96 to engage the septal wall W or other tissue proximate the hole H to be occluded. In some embodiments, one or more barbs 104 is pointed or cone shaped. In the illustrated embodiment, the arm assembly 98 has six arms 102 although the disclosure is not to be limited to a certain number of arms 102.

It is also envisioned that the tip assembly 50 can be releasably connected to the distal support shaft 88 in other ways. For example, the tip assembly 50 can be releasably connected to the distal support shaft 88 with a connecting member (not shown) having a break force that is greater than the force required to deploy the arms 102 and draw the barbs 104 into the tissue or septal wall W. Once the barbs 104 are engaged with the tissue to occlude the hole, force can be allied to the connecting member to disconnect the tip assembly 50 from the remaining portion of the delivery device 40. Alternatively, it is envisioned that one or more sutures (not shown) can be used to selectively connect and disconnect the tip assembly 50 from the distal support shaft 88. The sutures can be cut, for example, to release the tip assembly 50 from the remaining portion of the delivery device 40.

Figure 9:
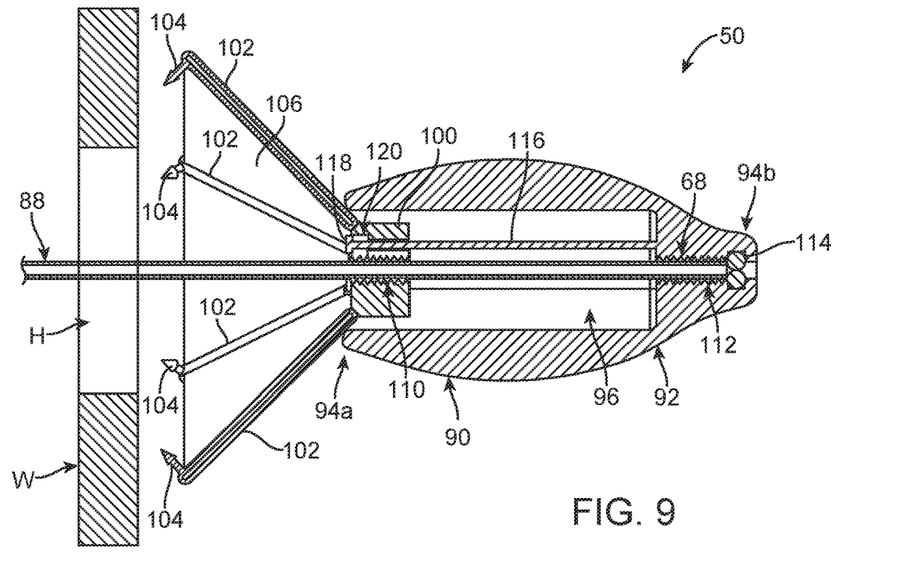
FIG. 9 is a side, cross-sectional view of the tip assembly of FIG. 5 adjacent a hole in the septal wall; wherein the arm assembly is drawn proximally toward the septal wall to position the tip assembly in a partially-deployed state.
Figure 10:
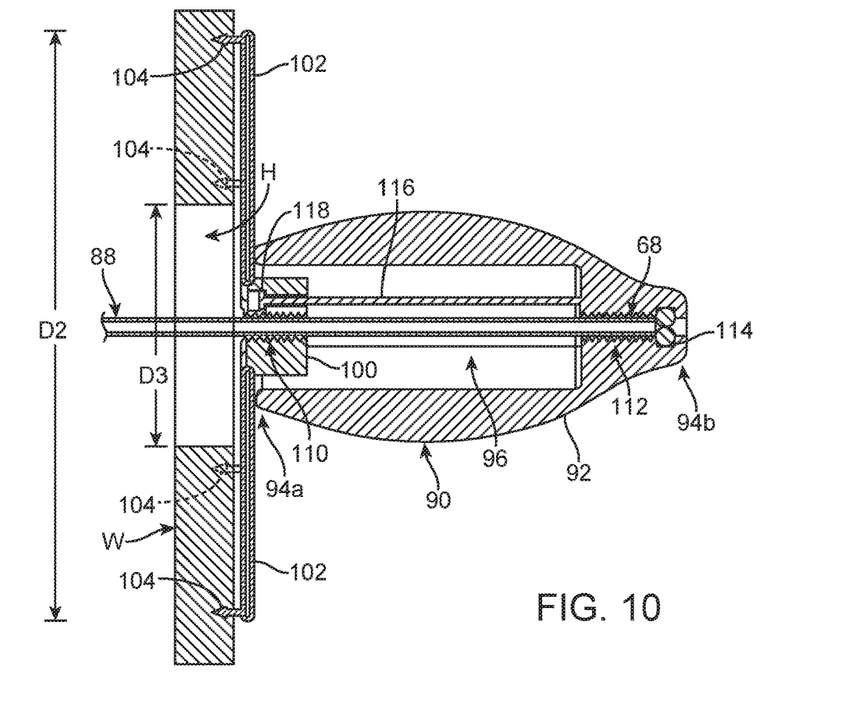
FIG. 10 is a side, cross-sectional view of the tip assembly of FIG. 5 in which the arm assembly has been further drawn proximally to engage the septal wall in a deployed state.

Once the prosthetic valve 10 is deployed at a target site (e.g., at the mitral valve MV), the delivery device 40 is retraced to position the tip assembly 50, while in the delivery state, in the left atrium LA, adjacent the hole H as is generally shown in FIG. 9. If the delivery device 40 includes the delivery sheath assembly 42, the delivery sheath assembly 42 is retracted slightly via the handle assembly 48 or the like to position the delivery device 40 in a valve deployment arrangement. In both the loaded arrangement and the valve deployment arrangement, the tip assembly 50 is in the delivery state. Then, the support shaft assembly 44 is advanced via the handle assembly 48 or the like and a pull-wire (not shown) is activated to pull the ring 100 outside of the cavity 96. Once freed from the confines of the cavity 96, the arms 102 and skirt 106 self-revert and pivot away from a central axis A of the ring 100 to expand outwardly into the partially-deployed state. The pull-wire is further pulled proximally in tension via handle assembly 48 or the like so that the barbs 104 on the arms 102 engage the septal wall W proximate the opening to implant the tip assembly 50 in the septal wall W as is generally shown in FIG. 10. Then the support shaft assembly 44 (including distal support shaft 88) can be retracted from the threaded tip 68 and into the threaded ring 100 for a final retraction to confirm the barbs 104 are fully seated. In this deployed state, the arms 102 are transversely arranged and a maximum outer diameter D2 of the tip assembly 50 in the deployed state is greater than the diameter D3 of the hole H in the septal wall W so that the tip assembly 50 is capable of occluding the hole H. The support shaft assembly 44 is then detached from the ring 100 to completely disconnect the distal support shaft 88 from the tip assembly 50 via methods outlined above, for example.

The delivery devices, systems and methods of the present disclosure provide a marked improvement over previous designs. By providing the delivery device having a tip assembly that can be used to close any septum holes after deployment of the prosthetic heart valve, procedure time and complexity is reduced.

Although the present disclosure has been described with reference to preferred embodiments, workers skilled in the art will recognize that changes can be made in form and detail without departing from the spirit and scope of the present disclosure. For example, while the devices and systems of the present disclosure have been described as being useful for delivering a stented prosthetic heart valve, a number of other implantable devices can be employed.

What is claimed is:

1. A delivery device for implanting a stented prosthetic heart valve, the device comprising:
   a support shaft having a distal region;
   a retention assembly associated with the support shaft and configured to retain the stented prosthetic heart valve; and
   a tip assembly releasably coupled to the distal region of the support shaft distal to the retention assembly;
   wherein the delivery device is configured to permit in vivo release of the stented prosthetic heart valve and, in a separate action, actuate in vivo release of the tip assembly from a remainder of the delivery device.

2. The delivery device of claim 1, wherein the tip assembly is configured to transition from a delivery state to a deployed state, and further wherein a maximum outer diameter of the tip assembly in the deployed state is greater than the maximum outer diameter in the delivery state.

3. The delivery device of claim 2, wherein the tip assembly is configured to engage tissue in the deployed state.

4. The delivery device of claim 2, wherein the tip assembly is configured for implantation over a hole in a septum of a heart when in the deployed state and released from a remainder of the delivery device.

5. The delivery device of claim 1, wherein the tip assembly includes:
   a housing defining a proximal side, a distal side, and a cavity; and
   an arm assembly slidably connected to the housing;
   wherein the tip assembly is configured to transition from a delivery state to a deployed state, and further wherein the delivery state includes at least a majority of a length of the arm assembly disposed within the cavity, and the deployed state includes at least a majority of the length of the arm assembly projecting from the housing outside of the cavity.

6. The delivery device of claim 5, wherein the housing defines a maximum outer diameter of the tip assembly in the delivery state and the arm assembly defines a maximum outer diameter of the tip assembly in the deployed state, and further wherein the maximum outer diameter of the tip assembly in the deployed state is greater than the maximum outer diameter of the tip assembly in the delivery state.

7. The delivery device of claim 5, wherein the arm assembly includes a plurality of arms, and further wherein the arms are longitudinally arranged in the delivery state, and even further wherein the arms are transversely arranged in the deployed state.

8. The delivery device of claim 5, wherein the arm assembly includes a plurality of arms and a plurality of barbs, and further wherein at least one of the barbs is attached to and extends from a respective one of the arms.

9. The delivery device of claim 8, wherein the delivery state includes the barbs disposed within the cavity, and further wherein the deployed state includes the barbs located outside of the cavity for engaging tissue.

10. The delivery device of claim 5, wherein the arm assembly includes a plurality of arms maintaining a skirt.

11. The delivery device of claim 10, wherein the tip assembly further includes a seal carried by the housing.

12. The delivery device of claim 1, wherein the tip assembly includes a housing that is generally conically-shaped.

13. A system for treating a defective heart valve via a trans-septal approach, the system comprising:
   a delivery device including:
      a support shaft having a distal region,
      a retention assembly associated with the support shaft, and
      a tip assembly releasably coupled to the distal region of the support shaft; and
   a stented prosthetic heart valve compressed over the support shaft and retained by the retention assembly in a loaded arrangement of the delivery device;
   wherein the delivery device is configured to permit in vivo release of the stented prosthetic heart valve and the tip assembly from a remainder of the delivery device.

14. The system of claim 13, wherein the delivery device includes an outer sheath; further wherein the delivery device transitions from the loaded arrangement in which a distal end of the outer sheath is proximal to the tip assembly and over the stented prosthetic heart valve to a valve deployment arrangement in which a distal end of the outer sheath is proximal the stented prosthetic heart valve to permit deployment of the prosthetic heart valve from the delivery device.

15. The system of claim 14, wherein the tip assembly is configured to transition from a delivery state to a deployed state, and further wherein a maximum outer diameter of the tip assembly in the deployed state is greater than the maximum outer diameter in the delivery state, and even further wherein the tip assembly is in the delivery state in both the loaded arrangement and the valve deployment arrangement.

16. The system of claim 15, wherein the tip assembly is configured for implantation over a hole in a septal of a heart when in the deployed state and released from a remainder of the delivery device.

17. The system of claim 13, wherein the tip assembly includes:
   a housing defining a proximal side, a distal side, and a cavity; and
   an arm assembly slidably connected to the housing;
   wherein the tip assembly is configured to transition from a delivery state to a deployed state, and further wherein the delivery state includes at least a majority of a length of the arm assembly disposed within the cavity, and the deployed state includes at least a majority of a length of the arm assembly projecting from the housing outside of the cavity.

18. A method of treating a defective heart valve of a patient, the method comprising:
   providing a delivery device including a support shaft maintaining a stented prosthetic heart valve and having a tip assembly adjacent and distal to the prosthetic heart valve;
   forming a hole in a septum of a heart of the patient;
   directing the tip assembly and the stented prosthetic heart valve through the hole;
   deploying the prosthetic heart valve from the delivery device to implant the prosthetic heart valve at the defective heart valve; and
   implanting the tip assembly at the hole in the septum.

19. The method of claim 18, wherein the step of implanting the tip assembly includes transitioning the tip assembly from a delivery state to a deployed state, a maximum outer diameter of the tip assembly in the delivery state being less than a diameter of the hole and a maximum outer diameter of the tip assembly in the deployed state being greater than the diameter of the hole.

20. The method of claim 18, further comprising the step of releasing the tip assembly from the support shaft after implanting the tip assembly.

* * * * *